United States Patent [19]
Dorian et al.

[11] Patent Number: 5,639,467
[45] Date of Patent: Jun. 17, 1997

[54] ELECTROSTATIC PROCESS FOR MANUFACTURING COATED TRANSPLANTS AND PRODUCT

[75] Inventors: Randel E. Dorian, Orinda; Kent C. Cochrum, Davis, both of Calif.

[73] Assignee: The Regents of the University of California, Oakland, Calif.

[21] Appl. No.: 422,032

[22] Filed: Apr. 14, 1995

Related U.S. Application Data

[63] Continuation-in-part of Ser. No. 890,982, May 29, 1992, abandoned, and a continuation-in-part of PCT/US93/05090, Jun. 1, 1993.

[51] Int. Cl.⁶ ..................................................... A61K 9/14
[52] U.S. Cl. .......................... 424/422; 424/550; 424/556; 424/491; 536/3
[58] Field of Search ................................. 424/550, 556, 424/422; 536/130, 3

[56] References Cited

U.S. PATENT DOCUMENTS

| | | | |
|---|---|---|---|
| 3,962,383 | 6/1976 | Hagiwara et al. | 264/4 |
| 4,352,883 | 10/1982 | Lim | 435/178 |
| 4,407,957 | 10/1983 | Lim | 435/178 |
| 4,673,566 | 6/1987 | Goosen et al. | 424/19 |
| 4,689,293 | 8/1987 | Goosen et al. | 435/1 |
| 4,744,933 | 5/1988 | Rha et al. | 264/4.3 |
| 4,749,620 | 6/1988 | Rha et al. | 428/402.2 |
| 4,789,550 | 12/1988 | Hommel et al. | 424/493 |
| 4,956,128 | 9/1990 | Hommel et al. | 264/4 |

OTHER PUBLICATIONS

Thomas M.S. Chang, *Semipermeable Microcapsules*, Science, vol. 146, pp. 524–525, (Oct. 23, 1964).

Thomas M.S. Chang, et al., *Semipermeable Aqueous Microcapsules, I. Preparation and Properties*, Canadian Journal of Physiology and Pharmacology, vol. 44, pp. 115–128, (1966).

Klaus Mosbach, et al., *Entrapment of Enzymes and Microorganisms in Synthetic Cross-linked Polymers and their Application in Column Techniques*, Acta Chem. Scand. 20, No. 10, pp. 2807–2810, (1966).

Kjell Nilsson, et al., *A General Method for the Immobilization of Cells with Preserved Viability*, Applied Microbiology and Biotechnology, 47: pp. 319–326, (1983).

K. Nilsson, et al., *Entrapment of animal cells for production of monoclonal antibodies and other molecules*, Nature, vol. 30, pp. 629–630, (Apr. 14, 1983).

H. Gin, et al., *Agarose encapsulation of islets of Langerhans: reduced toxicity in vitro*, J. Micro Encapsulation, vol., No. 3, pp. 239–242, (1987).

Somesh C. Nigam, et al. *Techniques for Preparing Hydrogel Membrane Capsules*, Biotechnology Techniques, vol. 2, No. 4, pp. 271–276, (1988).

Marian L. Plunkett, et al., *Methods in Laboratory Investigation, An In Vivo Quantitative Angiogenesis Model Using Tumor Cells Entrapped in Alginate*, Laboratory Investigation, vol. 62, No. 4, pp. 510–517, (1990).

M.A. Nawab and S.G. Mason, The Preparation of Uniform Emulsions by Electrical Dispersion, *Journal of Colloid Science*: 13, pp. 179–187, (1953).

Primary Examiner—Neil S. Levy
Attorney, Agent, or Firm—Hana Verny

[57] ABSTRACT

An electrostatic process for coating a biological material with a uniform, continuous polymer layer by discharging a suspension of the biological material in a gellable coating polymer solution in a continuous stream through an orifice. The stream is attenuated to form droplets by maintaining an electrostatic voltage between the needle and the gelling solution which is sufficient to maintain an attraction of at least $1 \times 10^6$ newtons on the stream of liquid leaving the needle, and the droplets are collected in a gelling solution. A preferred product is pancreatic islets having a continuous, smooth coating of high polymannuronate non-fibrogenic alginate having a thickness of at least 10 μm.

23 Claims, 1 Drawing Sheet

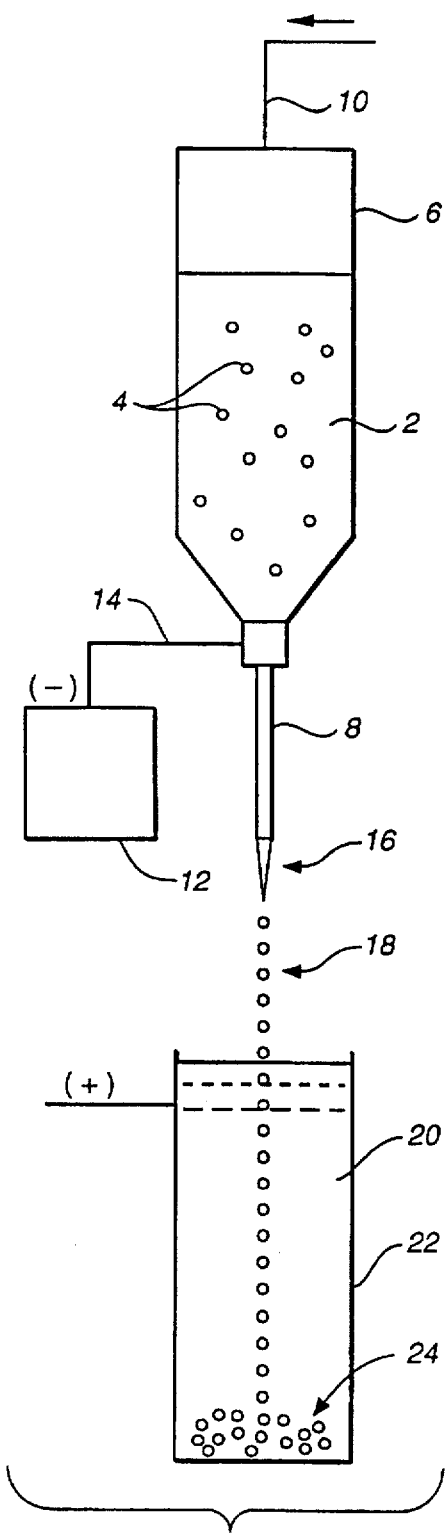
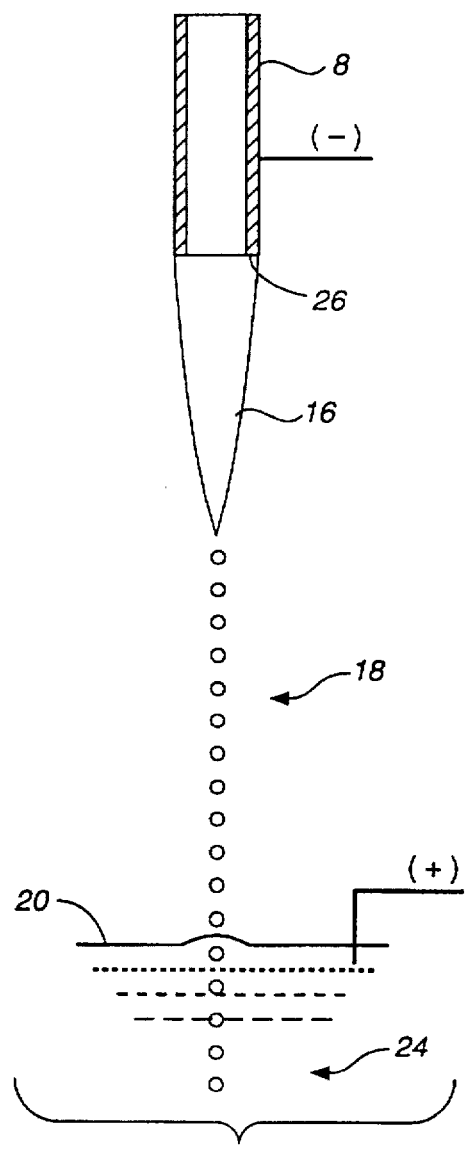
FIG._1        FIG._2

ELECTROSTATIC PROCESS FOR MANUFACTURING COATED TRANSPLANTS AND PRODUCT

This application is a continuation-in-part of U.S. application Ser. No. 07/890,982 filed May 29, 1992 and international Application No. PCT/US93/05090 filed on Jun. 1, 1993.

BACKGROUND OF THE INVENTION

1. Field of the Invention

This invention is directed to the field of medical transplants of cells and tissues, the manufacture of such transplants, and their use. In particular, this invention is directed to a process for forming thin, uniform, continuous coatings on tissue transplants such as pancreatic islet cells with a high degree of reproducibility.

2. Background and Related Disclosures

Traditional medical treatments for functional deficiencies of secretory and other biological organs have focused on replacing identified normal products of the deficient organ with natural or synthetic pharmaceutical compositions. For example, for treating insulin-dependent diabetes mellitus, also known as type I or juvenile onset diabetes, the normal secretion of insulin by the islets of Langerhans in the pancreas must be replaced since functional islets are no longer present in the pancreas. This pancreatic function is emulated by administering insulin, titrating the injections in response to blood glucose level measurements. At best, the normal production of the islets are poorly approximated.

Organ replacement has also been used. This has generally required continuous use of immunosuppressive agents to prevent immunological rejection of the organ, depriving the patient of the full protective function of the immune system against diseases. It has provided permanent relief only for a limited group of organs.

Attempts to transplant organ tissues into genetically dissimilar hosts without immunosuppression have been generally defeated by the immune system of the host. Prior to this invention, application of effective protective barrier coatings to isolate the transplant tissues from the host immune system has not proven to be medically practical for a number of reasons. The coating materials were incompatible with the host system or unsuitable for other reasons. Encapsulation or coating processes previously developed did not yield reproducible coatings having the desired permeability and thickness required for the transplant tissue to have a long and effective functioning life in the host.

To protect transplants from destruction by the immune response of the host animal, various attempts have been made to create a protective barrier between the transplant tissue or cells and the immunological components of the host's system. T. M. S. Chang, *Science*, 146:524–525 (1964) described the microencapsulation of erythrocyte hemolysate and urease in semi-permeable polyamide membranes. These microcapsules did not survive for long when injected into the blood stream. K. Mosbach et al, *Acta Chem. Scand.*, 20:2807–2812 (1966) and T. M. S. Chang et al, *Can. J. Physiol. and Pharmacol.*, 44:115–128 (1966) described the preparation of semi-permeable microencapsulated microbial cells and viable red blood cells, the latter article mentioning the possibility of using injections of encapsulated cella for organ replacement therapy.

Encapsulation methods applied to make these materials have comprised a procedure for forming droplets of the encapsulating medium and the biological material and a procedure for solidifying the encapsulating medium. Agarose encapsulated materials have been formed by chilling an emulsion of agarose droplets containing biological materials as shown by Nilsson et al, *Nature*, 302:629–630 (1983) and Nilsson et al, *Eur. J. Appl. Microbiol. Biotechnol.*, 17:319–326 (1983). Injection of droplets of polymer containing biological materials into a body of coolant such as a concurrently flowing liquid stream has been reported by Gin et al, *J. Microencapsulation*, 4:329–242 (1987).

Alginates form a gel when reacted with calcium ions. Alginate droplets have been formed by emulsifying a solution of sodium alginate containing cellular material to form droplets of sodium alginate and cells, and gelling the droplets with calcium chloride in U.S. Pat. No. 4,352,883. Alginate droplets have also been formed with a syringe and pump to force droplets from a needle, using a laminar flow air knife to separate droplets from the tip, the droplets being gelled by collecting them in a calcium chloride solution in U.S. Pat. No. 4,407,957. Alginate droplets have also been formed by the simple procedure of expelling them from a hypodermic needle and allowing the droplets to fall into a calcium chloride solution, as described by Nigam et al, *Biotechnology Techniques*, 2:271–276 (1988). Droplets have also been injected into a concurrently flowing stream containing calcium chloride in U.S. Pat. No. 3,962,383. Spraying alginate solutions through a spray nozzle to form a mist of droplets which were collected in a calcium chloride solution was reported by Plunkett et al, *Laboratory Investigation*, 62:510–517 (1990). These methods have not proven effective for mass production of coatings required for successful transplantation.

Hommel et al in U.S. Pat. No. 4,789,550 disclose the formation of alginate droplets using a combination of a needle and a square wave electrical electrostatic voltage to form uniform droplets. The alginate solution was forced from the tip of a needle to form a droplet, and the droplet was pulled from the needle by a changing electrostatic field between the needle tip and a calcium chloride solution placed below the needle tip. The droplet received a charge of one polarity from the needle, opposite to the charge in the calcium chloride solution. When the voltage difference between the droplet and the oppositely charged calcium chloride solution reached a value at which the attraction by the solution on the droplet exceeded the force of interfacial tension holding the droplet on the needle tip, the droplet was pulled free to fall into the calcium chloride solution. The electrostatic field was fluctuated using a square wave form to create a succession of voltages crossing the threshold voltage at which droplets were pulled free from the needle, thus producing a continuous series of droplets, one per square wave cycle. The process was not found to provide the small droplets and thin coatings required for effective transplantation.

SUMMARY OF THE INVENTION

It is one object of this invention to provide an apparatus and process which produces uniform, smooth, continuous coatings on transplantation tissues and cells, the coatings having a reproducible thickness of less than 200 µm.

It is another object of this invention to provide an apparatus and process which produces coatings of physiologically non-toxic, host-compatible materials on transplantation tissues and cells, the coatings having the permeability required for the diffusion of nutrients and biological materials required for the long life and effective function of the transplanted tissues and cells in the transplant host, while providing effective protection to the transplanted tissues from the host immune system.

In summary, the process of this invention is a procedure for coating a biological material with a uniformly sized coating of polymer comprising the steps of dispersing the biological material in an aqueous solution of the polymer. The suspension is released from an orifice in a continuous stream above an electroconductive liquid capable of gelling the polymer. At the same time a first voltage is applied to the orifice and a second voltage is applied to the electroconductive liquid. The electric voltage between the orifice and the electroconductive liquid and the electric charge of the released droplets attenuate the stream of aqueous solution to form a continuous stream of droplets having a reproducible size. The droplets are then gelled by collecting the droplets in the electroconductive liquid to form particles with a continuous, smooth polymer coating on the biological material. Preferably, the polymer solution has a viscosity of from about 10 to about 250 centipoises and the orifice has a diameter of from about 0.1 to 2 mm.

In a preferred embodiment, the polymer solution is a sodium alginate solution, and the electroconductive liquid is an aqueous electrolyte solution containing a concentration of calcium ions sufficient to gel the alginate.

The voltage difference between the orifice and the electroconductive liquid is sufficient to provide a continuous attraction for the liquid leaving the needle of at least $1 \times 10^{-6}$ newtons.

The coated products of this process are a further aspect of this invention. These are preferably coated cores of viable, physiologically active, tissue cells such as pancreatic islet cells having a non-fibrogenic coating of alkaline earth metal alginate coating thickness of from about 10 to about 200 μm.

BRIEF DESCRIPTION OF THE DRAWINGS

FIG. 1 is a schematic representation of the electrostatic apparatus of this invention.

FIG. 2 is an enlarged schematic representation of the liquid stream showing the stream attenuation and drop formation in the electrostatic apparatus of this invention.

DETAILED DESCRIPTION OF THE PREFERRED EMBODIMENTS

The apparatus and process of this invention is highly effective for applying uniform, continuous, smooth coatings on transplantation tissue cells with a high degree of control and reproducibility and at coating rates which are medically practical. The coated products have the effective volumes and diameters required for transplantation by injection through standard needle gauges.

The term "transplant", as used herein, is defined to include all living tissues, cells, and biologically active substances or material intended to be implanted into the body of a host animal and the act of implanting these tissues and cells. These tissues and cells include, without limitation, tissue and cells removed from a donor animal, tissue and cells obtained by incubation or cultivation of donor tissues and cells, cells obtained from viable cell lines, biologically active products of cells and tissues, and the like.

Any type of tissue or cells for which transplantation is desired can be coated and transplanted according to this invention. The most important tissues for transplants are secretory organ tissues, where transplantation from a donor organ to a host animal is desired to at least partially replicate the donor organ's action in the host system. Preferred donor tissues are pancreatic islets, hepatic cells, neural cells, renal cortex cells, vascular endothelial cells, thyroid cells, adrenal cells, thymic cells and ovarian cells. Transplants can be allographs or xenographs.

For secretory tissues such as pancreatic islets, the thickness of protective porous coatings is in the range of from about 10 to about 200 μm. The coatings must also have the permeability required to permit effective diffusion of nutrients and other essential biological materials to the transplanted tissues and passage of transplant tissue products therefrom into the host or donor system. The coatings must simultaneously exclude immunologically effective concentrations of agents of the host immune system from the transplant tissue.

The apparatus of this invention will produce transplant tissue coatings having these essential characteristics with high efficiency and product volumes required to replace or supplement an organ's function in a human host.

Referring to the drawings, FIG. 1 is a schematic representation of the electrostatic apparatus of this invention, and FIG. 2 is an enlarged schematic representation of the liquid stream showing the stream attenuation and drop formation in the electrostatic field created by the apparatus. A coating solution 2 containing electrolytes and suspended transplant tissue fragments or cells 4 is provided in a reservoir 6. An orifice outlet for a thin stream of coating solution is provided by needle 8 communicating with the liquid in the reservoir. Pressure for expelling liquid from the reservoir 6 through the needle 8 can be provided by any conventional system, such as a gas pressure supply line 10 or alternatively, a plunger, pump or other conventional system.

An electrostatic voltage is applied to the metal needle 8 or to the solution from a conventional high DC voltage source such as a van de Graaff generator or other conventional high voltage DC power supply 12 through electrical connection 14. The voltage must be constantly at a level sufficient to continuously form an attenuated stream of suspension 16 forming a continuous series of droplets 18 having a constant size. The droplets are collected in a solution 20 contained in droplet collector 22, the solution 20 having a charge opposite to the charge of the needle 8. Solution 20 provides the reagents or conditions required to solidify the droplets, forming the coated transplantation products 24.

In the embodiment shown in FIG. 1, the needle has a negative charge and the electroconductive collection container 22 has a positive charge. It will be readily apparent to a person skilled in the art that alternative configurations can be provided to yield a high voltage electrostatic potential of opposite charges between the needle 8 and the solution 20. For example, the polarities can be reversed, and the needle 8 can have a positive charge relative to the solution 20.

Without the electrostatic attraction of the solution 20 for the liquid leaving the needle 8, large individual droplets would be formed, their size being determined only by gravitational force, the interfacial tension of the solution and the flow rate, yielding a coating with excessive thickness. We have found that coatings of the desired size can be obtained when the continuous attraction of the solution 20 for the liquid leaving the needle is at least about $1 \times 10^{-6}$ newtons for coating solutions having a viscosity of from about 10 to 250, preferably 20–100 centipoises. In prior art processes, needle size must be reduced to produce smaller droplets, requiring increased pressures and placing a practical lower limit on the sizes which can be obtained. Since the particle sizes produced by the process of this invention are independent of the needle size, the smallest particles can be produced, even with the largest needles. This permits small particles to be formed from viscous solutions with a minimum of pressure.

For needle orifices 8 having inner diameters of from about 0.1 to about 2 mm, electrostatic DC voltages of from about 1 to about 400 KV have been found to be satisfactory for operation in air under ambient conditions. Currents ranging from about 0.2 µA to about 10 µA are suitable.

The process of this invention for coating a biological material such as transplant tissues with a uniformly sized coating of polymer using the apparatus described above comprises dispersing the biological material in an aqueous solution of the polymer 2. Then the aqueous solution is discharged from an orifice 8 in a continuous stream 16 above an electroconductive liquid 20 capable of gelling the polymer while placing an electrical charge of one polarity on the stream while it is being discharged. An electric charge of opposite polarity is maintained on the electroconductive liquid 20, the electric charge being sufficient to continuously attenuate the stream of aqueous solution to form a continuous stream of droplets having a reproducible size. The polymer droplets are then gelled to form a continuous polymer coating on the biological material and smoothing the coating to form spherical coated particles by collecting the droplets in the electroconductive liquid 20. Preferably, the polymer solution has a viscosity of from about 10 to about 250 centipoises, and the orifice has a diameter of from about 0.2 to 0.8 mm.

This process can be used to coat any transplant of biologically active agents, tissues or cells. It is particularly advantageous for coating transplantation tissues such as pancreatic islets, hepatic cells, other endocrine tissues and cells, and neural cells.

Coating agents must be physiologically acceptable and non-toxic to the biologically active material being coated and to the host or recipient organism and its tissue. The coating must be non-fibrogenic to avoid encapsulation by the host immune system. Coatings having an outer negative charge, such as polysaccharides (agarose, etc.) and alginates, are most suitable. Particularly effective coating materials are the highly purified alginates.

To prepare the non-fibrogenic alginate of the invention, an initial alginate preparation is dissolved in water or a buffer, preferably containing a divalent metal ion chelating compound such ethylenediamine tetraacetic acid (EDTA), and then contacted with a high surface area activated carbon to remove fucans and other contaminants by adsorption. Fifty grams of alginate is usually dissolved in about 1–10, preferably in about 3–8 liters of water. Suitable activated carbon includes any high surface area activated carbon having a particle size of about 100 mesh or finer. Preferably, very fine activated carbon powder having a surface area of at least 1,000, preferably at least 1,500 $m^2/g$ is used. Suitable activated carbon is commercially available.

The activated carbon is preferably bleached to oxidize and remove organic contaminants prior to use. The activated carbon may be bleached using a known bleaching agent such as sodium hypochlorite. The carbon is bleached by stirring with a dilute solution of the bleach for a time sufficient to remove any contaminants from the surface of the carbon. Generally, stirring the activated carbon with about 0.005–0.50M, preferably about 0.08–0.10M, sodium hypochlorite solution for about 5–30, preferably about 10–20 minutes, is sufficient to oxidize the activated carbon. After oxidation, the activated carbon is removed from the dilute bleach solution by centrifugation or filtration, washed with water or ethanol and dried. The ratio (w/w) of initial alginate to activated carbon is usually from about 1:1 to about 1:20, preferably from about 1:2 to about 1:8. Obviously, the amount of activated carbon can be adjusted as necessary to insure removal of contaminants to achieve the minimum amounts required for this invention.

The alginate solution and bleached carbon may be contacted by simple mixing, shaking or rolling, and the bleached carbon is then removed by conventional centrifugation and filtration. Preferably, the filtration is conducted using sequentially finer sub-micron filters.

A dilute monovalent cation salt solution is then added to the filtered alginate solution in an amount sufficient to exchange metal ion binding sites on the alginate. Any soluble monovalent cation salt may be used, however sodium or potassium chloride solutions of about 0.01–1.0M are preferred.

Alginate is then precipitated from the resulting solution by addition of ethanol with stirring. Generally, the ratio (v/v) of ethanol to alginate solution is about 0.25–2.0, preferably about 0.5–1.5. The precipitated alginate is then recovered by filtration, washed with ethanol and dried to remove traces of ethanol.

The alginate obtained as described above is directly suitable for coating a transplant tissue or cells without the use of additional coating compounds such as homopolyamino acids, e.g. polylysine or polyaspartic acid. However, it is sometimes desirable to chemically modify the properties of the alginate to tailor the alginate coating for specific uses. Important properties of alginate coating materials include: a well defined and controlled pore size, coating thickness, viscosity of coating solutions, mechanical strength, etc.

Average molecular weight and overall mannuronate to guluronate molar ratios are initially determined substantially by material origin but can be further adjusted by physical and chemical methods. Molecular weights can be reduced, for example, by partial acid hydrolysis, thermal degradation or sonication. High molecular weights can be obtained by controlled precipitation methods with concomitant alteration of alginate composition or by dialysis, molecular filtration, or gel exclusion chromatography. The mannuronate to guluronate ratio and sequence distribution can be increased or decreased by selective precipitation or solubilization by mono- and di-valent metal cations, organic solvents or acids. Adjustment of these characteristics provide optimum results with different tissue transplants.

The concentration of an alginate solution is a function of the physical properties of the alginate. At very low concentrations, coating morphology is poor resulting in ineffective coatings. At very high concentrations, viscosity is too high to form good coatings. Preferably, the molecular weight (kilodaltons) of the alginate is in the range about 2–300, more preferably about 4–250, even more preferably about 6–120. High initial molecular weights can be adjusted by mild acid hydrolysis of the alginate. The initial or purified alginate is dissolved in a dilute acid solution and gently heated until the desired molecular weight is obtained. Dilute solutions of mineral acids, such as HCl, having a concentration of about 0.1–0.5 M may be used. The degree of hydrolysis is controlled by monitoring the molecular weight of the alginate and neutralizing the hydrolysis reaction when the desired molecular weight is obtained. Obviously, higher acid concentrations result in faster hydrolysis. Alternatively, a few initial test reactions are usually sufficient to determine appropriate hydrolysis conditions.

The porosity and mechanical strength of the coating are also a function of the relative amounts of mannuronate (M) and guluronate (G) in the alginate polymers. Preferably, the amount of M, calculated as M/(M+G), in the alginate is in the range from about 0.1–0.95, more preferably from about 0.15–0.85, even more preferably from about 0.25–0.75. The relative amount of M and G in the alginate can be adjusted by dissolving precipitated alginate in a dilute (0.05–0.50M) potassium chloride solution to redissolve G-rich fractions leaving M-rich fractions in the precipitate. The insoluble material is collected by centrifugation. The redissolved G-rich material is then reprecipitated by addition of ethanol. By repeating this process, the desired relative proportion of M and G in the alginate is obtained.

Homopolymeric alginate sequences (polymannuronate and polyguluronate) are acid-insoluble, whereas alternating mannuronate-guluronate sequences are acid-soluble. By extracting the alginate with an acid solution of about pH 1.5–2.5, preferably about pH 2.0, it is possible to selectively solubilize homopolymeric-rich alginates. Additionally, M-rich alginates are preferentially solubilized relative to G-rich alginates. Treatment of an alginate with an acidic solution, therefore, precipitates G-rich alginates preferentially leaving M-rich alginates in solution. Separation of the precipitate from the solution provides both G-rich and M-rich alginate fractions. The G-rich alginates in solution can be obtained by precipitating the alginates from solution by addition of calcium ions or ethanol. Alternatively, G-rich alginate can be obtained by initial treatment with calcium ions resulting in precipitation of G-rich fractions leaving M-rich fractions in solution. After separation of the precipitate from the solution, the M-rich alginate fraction can be precipitated from solution by the addition of acid or ethanol. The proportions of acid and/or calcium precipitated materials can be controlled by adjusting the pH and calcium concentration, respectively.

It is also possible to obtain specific relative amounts of M and G in the coating alginate by mixing different M-rich fractions and G-rich fractions obtained as described above. By sequentially adding small portions of G-rich material to M-rich material, one gradually increases the amount of G in the overall alginate composition, thereby increasing divalent metal ion binding sites in the overall coating, increasing the structural rigidity of the coating and producing larger pore sizes. For any particular mixture of M-rich and G-rich fractions, the relative amount of M or G in the alginate can be readily determined by NMR spectroscopy. $^{13}$C-NMR spectroscopy is a rapid and inexpensive method for determining the M/G ratio and disaccharide sequence frequencies. In alternative, $^1$H-NMR may be used to determine M/G ratios. Mixing M-rich and G-rich fractions allows one to control the average molecular weight and porosity of the alginate coating.

The alginates of the present invention are non-fibrogenic, having a hydrolyzable fucose sugar content of 0.2 micrograms per milligram sodium alginate (0.02 wt %) or less, preferably less than 0.1 micrograms per milligram sodium alginate (0.01 wt %), even more preferably less than 0.05 micrograms per milligram sodium alginate (0.005 wt %). Fucose sugar levels in the alginates can be determined by conventional neutral sugar analysis such as described in Example 4.

The alginates of the present invention contain a non-fibrogenic amount of polyphenols, such as tannins or phloroglucinol. To determine the level of polyphenols in the alginate samples of the present invention, a novel assay was developed based on a standard method for measurement of tannin levels in water. See Hach's Water Analysis Handbook, Second Edition (1992), Method 8193, adapted from M. B. Kloster, Journal of the American Water Works Association, 66:44 (1974). Tannins are polyphenols and the novel alginate assay for polyphenols of this invention gives the polyphenol content in terms of tannic acid or "tannin-equivalents" based upon standard tannic acid solutions of known concentration.

In the present assay for polyphenols in alginates, the alginate samples are prepared at 1 wt % in water. An aliquot of the alginate sample is placed into a test tube and water is placed into a control test tube. A sodium carbonate solution and TANNIVER® 3 reagent (sodium tungstate, phosphoric acid, hydrochloric acid, anhydrous sodium molybdate, lithium sulfate, water plus 1% other reagents) are added to both the sample tube and control tube, the solutions are mixed and then incubated at room temperature for 30 minutes. The absorbance of cuvettes containing the sample and control tubes is then measured at 700 nm.

A suitable tannic acid standard curve can be prepared using tannic acid standard concentrations of varying over a range of 0.1–10 µg/ml. After correcting the absorbance of the sample cuvette by subtracting the absorbance of the control cuvette, the absorbance of the alginate sample can be plotted against a standard curve prepared from the standard tannic acid solutions to determine the number of micrograms of tannic acid per milligram of alginate sample or the micrograms of "tannin-equivalents" per milligram of alginate sample. When tested with the polyphenol/tannin assay described above, the alginates of the present invention are shown to contain 2.0 micrograms or less of tannin-equivalents per milligram sodium alginate (0.2 wt %). Preferably, the alginates contain 1.0 micrograms of tannin-equivalents or less (0.1 wt %), more preferably 0.75 micrograms of tannin equivalents or less (0.075 wt %) per milligram of sodium alginate.

The method of the present invention allows one to prepare an alginate gel coating as required for a protective barrier excluding immunologically effective concentrations of the host immune system agents from the tissue and having the permeability required to permit sufficient diffusion of nutrients and other substances to the transplants required for their long life and viability.

The viscosity of coating solutions of the alginates having a concentration of from about 0.7 to about 2.5 weight percent alginate have a viscosity of from 10 to 250 centipoises and preferably from about 20 to 100 centipoises at 25° C.

When the polymer solution is a sodium alginate solution, the solution 20 can be an aqueous, electroconductive alkaline earth metal salt solution such as an aqueous solution containing a level of calcium and/or magnesium ion sufficient to react with and gel the alginate coating. The calcium ion concentration, as calcium chloride, should be at least 0.5 weight percent of the solution.

When the polymer solution is an agarose solution, the droplets can be gelled by cooling with air and collected.

The products of this process are coated cores of viable transplant, i.e., physiologically active, living tissue or cells, such as pancreatic islet cells, having a coating thickness from 10 to 200 µm.

This invention is further illustrated by the following specific but non-limiting examples. Percents are given in weight percents and temperature in degrees centigrade unless otherwise specified.

EXAMPLE 1

Medium Guluronate Alginate Preparation

Low viscosity sodium alginate (LV Alginate, KELCO DIV. of Merck & Co.; 50 grams) isolated from Macrocystis pyrifera was dissolved in 5 liters of water and filtered through a 50 micron mesh to remove particulates. Disodium EDTA (18.6 grams) was added to the solution and dissolved. The solution was mixed on a roller mill with hypochlorite-bleached activated carbon (200 g; Mallinckrodt activated carbon powder) for 30 minutes to remove organic contaminants such as polyphenols and fucose sugar residues. Activated carbon was then removed by centrifugation for 30 minutes. The resulting solution was sequentially filtered through filter paper, a 0.45 micron filter, a 0.22 micron filter and a 0.1 micron filter. Sodium chloride (30 g) was then added to the filtered solution and dissolved by rolling on a roller mill. The alginate was precipitated from solution by the addition of neat ethanol (5 liters). The sample was centrifuged for 30 minutes to obtain an alginate pellet. The alginate pellet was suspended in ethanol and then teased apart with tweezers to insure complete washing of the sample. Excess ethanol was removed by squeezing and pressing the precipitate.

The resulting precipitate was dried in an oven, under vacuum, at 60° C.

EXAMPLE 2

High Guluronate Alginate Preparation

Protan alginate (80 g) was dissolved in 8 liters of water by rolling on a roller mill. The solution was filtered through a 50 micron mesh to remove particles and then mixed on a roller mill with 320 grams of bleached, activated carbon with continued mixing for 30 minutes. The activated carbon was then removed by centrifugation for 30 minutes. The resulting solution was sequentially filtered through filter paper, a 0.45 micron filter, a 0.22 micron filter and a 0.1 micron filter. Magnesium chloride (163 g) was then added to the solution and dissolved by rolling on a roller mill. A calcium chloride solution (210 ml of a 1.7% solution) was then added and mixed by rolling on a roller mill for 30 minutes. The resulting solution was centrifuged for 30 minutes to produce an alginate pellet. The alginate pellet was dissolved in 3.0 liters of 0.1M EDTA (pH 7.0) by rolling on a roller mill. The pH of the solution was adjusted to pH 7.0 as needed. Sodium chloride (20 g) was then added to this solution and dissolved.

Alginate was precipitated from the solution by the addition of 5 liters of neat ethanol, followed by centrifugation for 30 minutes to obtain an alginate pellet. The alginate pellet was suspended in ethanol and tweezed apart with tweezers to insure complete washing of the sample. Excess ethanol was then removed by squeezing and pressing the precipitate.

The alginate precipitate was then dried in an oven, under vacuum, at 60° C.

EXAMPLE 3

Fucose and Tannin

Equivalent Content Determination

Standard tannic acid solutions were prepared by diluting a freshly prepared tannic acid solution (0.1 mg/ml) to obtain standard solutions having a concentration of 10.0, 5.0, 3.0, 1.0, 0.4 and 0.1 µg/ml. A tannic acid standard curve was then prepared by plotting the concentration of tannic acid against the absorbance of each sample read at 700 nm in a spectrophotometer.

Sample solutions of the alginates of Examples 1 and 2 were prepared at 1 wt %. A 2 ml aliquot of each sample was placed into a 5 ml test tube. Two ml of water were placed into a test tube as a control. Sodium carbonate solution (0.4 ml of Hach Cat. 675-49) was then added to each tube, including the control. TANNIVER® 3 reagent (0.04 ml) was added to each tube and thoroughly mixed. The tubes were then incubated at room temperature for 30 minutes. The sample was transferred to a quartz cuvette, and the absorbance read at 700 nm in the spectrophotometer. After correcting for the absorbance of the sample blank cuvette, the absorbance of each alginate solutions was plotted against the tannic acid standard curve to determine the number of micrograms of tannic acid equivalents per milligram of sodium alginate sample. The alginate of Example 1 was found to contain 1.0 micrograms of tannic acid equivalents per milligram of sodium alginate (0.1 wt %). The alginate of Example 2 was found to contain 0.7 micrograms of tannic acid equivalents per milligram of sodium alginate (0.07 wt %).

For comparison, the initial alginates used to prepare the alginates of Example 1 and Example 2 were assayed for polyphenol content using the polyphenol/tannic acid assay described above. Each of the initial alginates used to prepare the purified alginates of Examples 1 and 2 was found to contain about 2.0 micrograms of tannic acid equivalents per milligram of alginate. The purification process of Example 1 provides a reduction in tannic acid equivalents of greater than 90%; the process of Example 2 provides a reduction in tannic acid equivalents of greater than 90% relative to the initial alginate compositions. The process of the present invention is effective in substantially reducing the level of polyphenols in the initial alginates.

EXAMPLE 4

Fucose Sugar Analysis

The content of fucose in alginate samples can be determined by gas chromatography-mass spectrometry (GC-MS) analysis. To prepare samples for GC-MS analysis, 1–3 mg of each sample was weighed and placed in a screw top (100 mm×13 mm) test tube. $H_2SO_4$ (0.5 ml at 1N) containing 50 µg inositol as an internal standard was then added to each tube. Standard tubes containing 10.0, 1.0, 0.1 and 0.01 µg fucose were then prepared in a similar manner.

All tubes were heated for 1 hour (or 3 hours) at 121° C. After heating, the tubes were cooled and a stoichiometric quantity of barium chloride was added. The neutralized tubes were centrifuged (10 min, 1500×g) to remove the barium sulfate produced. Water remaining in the samples was evaporated under an air stream.

The samples were then reduced with sodium borohydride (1 mg/ml $NaBH_4$ in 1N $NH_4OH$, 0.5 ml solution, 1 hour at room temperature). After reduction, excess borohydride was decomposed by addition of 200 microliters of glacial acetic acid and evaporated under an air stream.

The reduced samples were acetylated using 200 microliters of acetic anhydride and 20 microliters of 1 methylimidazole (10 min at room temperature). The samples were then partitioned between 2 ml water and 2 ml methylene chloride. The water phase was removed and the remaining organic phase was evaporated. Fifty microliters of acetone were then added to each sample and an aliquot of the sample was injected into a 5890 HP gas chromatograph coupled to a 5970 HP mass selective detector. The GC separation was performed by a J & W DB-23 column (30 meters, 0.25 mm I.D.) using a temperature gradient running from 160° to 210° C. at 3°/min. MS analysis was performed by comparison of retention times and of spectral comparisons with authentic standards.

The results of fucose analysis for the initial alginates and purified alginates of Examples 1 and 2 are shown in the table below.

| SAMPLE | FUCOSE (μg fucose/mg sample) |
|---|---|
| Ex. 1 (initial) | 2.91 (0.291 wt %) |
| Ex. 1 (purified) | <.01 (<0.001 wt %) |
| Ex. 2 (initial) | 0.70 (0.07 wt %) |
| Ex. 2 (purified) | 0.09 (0.009 wt %) |

The fucose level in sample Ex. 1 (purified) is reduced by a factor of more than 300 relative to the fucose level in Ex. 1 (initial); the fucose level in alginate Ex. 2 (purified) is reduced by a factor of 8 relative to Ex. 2 (initial).

EXAMPLE 5

Pancreatic Suspension Islet Preparation

Pancreatic islets isolated from rat were washed with isotonic saline and suspended in an alginate solution prepared by dissolving the alginate prepared by the procedures of Example 1 and Example 2 at a concentration of 10,000 islets per ml in 1.9 wt % purified alginate in 10 mM HEPES, 0.01M sodium citrate, containing sufficient sodium chloride required for isomolarity (about 0.81 wt %), the final solution having a viscosity of about 50 centipoises at 32° C. The islets had an approximate average diameter of 150 μm. This procedure was repeated with dog islets.

EXAMPLE 6

Pancreatic Islet Coating

Using a DC electrostatic voltage of 8 KV provided by a van de Graaff generator between needle tip and grounded 0.117M aqueous calcium chloride solution at ambient temperature, a suspension of pancreatic islets (25 islets per μL) prepared by the procedure of Example 5 was passed through a 20 gauge needle at a flow rate of approximately 200 μl/min. The suspension emerged from the needle as a thin, attenuated stream which transformed into droplets, the droplets being collected in the calcium chloride solution. The droplets were gelled by reaction with the calcium ion in the solution. The calcium alginate coatings on the islets were smooth and uniform and had an approximate thickness of about 130 μm. The total coated particle had an average diameter of about 360 μm.

This process was repeated with dog islets prepared by the procedure of Example 5.

EXAMPLE 7

Pancreatic Islet

Transplant into Diabetic Mice (IP)

Host Balb/C mice were rendered diabetic by IP injection of streptozocin (250 mg/kg) at 50 mg/mL in 0.1M citrate buffer, pH 4.5 several days prior to transplant.

Coated dog islets prepared by the procedure of Example 6 were injected IP. 2000–3000 islets per mouse, into one group of mice. The mice became and remained euglycemic for over 72 weeks (18 months). These mice were sacrificed and the coated islets examined. The alginate-coated islets were found to be viable, free from fibrosis and free from macrophage overgrowth (only 2–10 macrophages per coated islet capsule).

Spheres formed from the same alginate (without cells) were injected IP into a control group of Balb/C mice. The mice were sacrificed at intervals for periods of a few days to several weeks. The alginate spheres were examined histologically and found to be free from fibrosis and substantially free from macrophage overgrowth.

Numerous modifications and variations of the present invention are possible in light of the above teachings. It is therefore to be understood that within the scope of the appended claims, the invention may be practiced otherwise than as specifically described herein.

What is claimed is:

1. A process for producing a pancreatic islet, tissue or cell transplant coated with a non-fibrogenic alginate polymer coating having a uniform thickness from about 20 μm to about 200 μm, said process comprising the steps:
   (a) preparing a non-fibrogenic alginate containing less than 0.02 wt % fucose and less than 0.2 wt % of polyphenol by:
      (1) dissolving a nonpurified alginate polymer having a molecular weight from about 2 to about 300 kDa and a weight to weight ratio of mannuronate to mannuronate/guluronate (M/M30 G) from about 0.1 to about 0.95, in an aqueous solution;
      (2) contacting said solution with a high surface area absorbent able to remove fucans and polyphenols;
      (3) separating the alginate polymer from the absorbent;
      (4) contacting the alginate polymer in solution with a monovalent cation; and
      (5) precipitating the alginate polymer from the solution;
   (b) preparing an aqueous solution of the non-fibrogenic alginate precipitate of step (a);
   (c) dispersing the pancreatic tissue or cells in the solution of step (b) to form a suspension having a viscosity from about 50 to about 150 centipoises;
   (d) transferring the suspension of step (c) to an electrostatic apparatus comprising a reservoir, an extrusion needle, an electroconductive droplet collector and a means for generating electrostatic field of opposite charge, said reservoir being used for holding the suspension and being in communication with the extrusion needle, said needle positioned above the electroconductive droplet collector containing a gelling solution, said means for generating electrostatic field being able to generate a sufficient electrostatic voltage to maintain the attenuated stream of the suspension due to an opposite charge between the extrusion needle and between the droplet collector;
   (e) generating a DC electrostatic voltage level sufficient to maintain the attenuated stream of the suspension to form a continuous series of the charged droplets wherein said voltage is being generated between the needle tip and between the container holding the gelling solution;
   (f) extruding the suspension of step (c) through an extrusion needle tip having an end orifice diameter of from about 0.1 to about 2 mm, in an attenuated stream into the gelling solution and solidifying the alginate polymer of step (c) to form the droplets having constant and reproducible size;
   (g) maintaining said voltage level during the whole time of formation of the droplets to provide an electrostatic attraction of the gelling solution for the charged droplets;
   (g) collecting the droplets coated with a gelled and solidified non-fibrogenic alginate of from about 20 μm to about 200μ thickness as the transplants.

2. The process of claim 1 wherein the alginate polymer is dissolved in water or buffer containing a divalent metal ion chelating compound.

3. The process of claim 2 wherein the chelating compound is ethylenediamine tetraacetic acid.

4. The process of claim 3 wherein a high surface area absorbent able to remove fucans and polyphenols is an activated carbon having a particle size of about 100 mesh and a surface area of about 1000 to 1500 m²/g.

5. The process of claim 4 wherein the ratio of the nonpurified alginate to the activated carbon is from about 1:1 to about 1:20.

6. The process of claim 5 wherein the non-fibrogenic alginate is separated from the absorbent by centrifugation or filtration.

7. The process of claim 6 wherein the non-fibrogenic alginate is contacted with a dilute solution of a monovalent cation salt from which the alginate is precipitated with ethanol.

8. The process of claim 7 wherein the monovalent cation salt is sodium chloride or potassium chloride.

9. A process for manufacturing a transplant comprising living tissue, cell, biologically active substance or biologically active material coated with a non-fibrogenic alginate coating, said process comprising steps:
 (a) preparing a non-fibrogenic alginate containing less than 0.02 wt % fucose and less than 0.2 wt % of polyphenol in terms of tannic acid;
  (1) by dissolving a nonpurified alginate polymer having a molecular weight from about 2 to about 300 Kda and a weight to weight ratio of mannuronate to manmannuronate/guluronate (M/M+G) from about 0.1 to about 0.95, in an aqueous solution;
  (2) contacting said solution with a high surface area absorbent able to remove fucans and polyphenols;
  (3) separating the alginate polymer from the absorbent;
  (4) contacting the alginate polymer in solution with a monovalent cation; and
  (5) precipitating the alginate polymer from the solution;
 (b) preparing an aqueous solution of the non-fibrogenic alginate precipitate of step (a);
 (c) dispersing the tissue, cells, substance or material to be coated in the solution of step (b) to form a suspension having a viscosity from about 50 to about 150 centipoises;
 (d) transferring the suspension of step (c) to an electrostatic apparatus comprising a reservoir, an extrusion needle, an electroconductive droplet collector and a means for generating electrostatic field of opposite charge, said reservoir being used for holding the suspension and being in communication with the extrusion needle, said needle positioned above the electroconductive droplet collector containing a gelling solution, said means for generating electrostatic field being able to generate a sufficient electrostatic voltage to maintain the attenuated stream of the suspension due to an opposite charge between the extrusion needle and between the droplet collector;
 (e) generating a DC electrostatic voltage level sufficient to maintain the attenuated stream of the suspension to form a continuous series of the charged droplets wherein said voltage is being generated between the needle tip and between the container holding the gelling solution;
 (f) extruding the suspension of step (c) through an extrusion needle tip having an end orifice diameter of from about 0.1 to about 2 mm, in an attenuated stream into the gelling solution and solidifying the alginate polymer of step (c) to form the droplets having constant and reproducible size;
 (g) maintaining said voltage level during the whole time of formation of the droplets to provide an electrostatic attraction of the gelling solution for the charged droplets;
 (h) collecting the droplets coated with a gelled and solidified non-fibrogenic alginate of from about 20 μm to about 200μ thickness as the transplants.

10. The process of claim 9 wherein the alginate polymer is dissolved in water or buffer containing a divalent metal ion chelating compound.

11. The process of claim 10 wherein the chelating compound is ethylenediamine tetraacetic acid.

12. The process of claim 11 wherein a high surface area absorbent able to remove fucans and polyphenols is an activated carbon having a particle size of about 100 mesh and a surface area of 1000 to 1500 m²/g.

13. The process of claim 12 wherein the ratio of the nonpurified alginate to the activated carbon is from about 1:1 to about 1:20.

14. The process of claim 13 wherein the non-fibrogenic alginate is separated from the absorbent by centrifugation or filtration.

15. The process of claim 14 wherein the non-fibrogenic alginate is contacted with a dilute solution of a monovalent cation salt from which the alginate is precipitated with ethanol.

16. The process of claim 15 wherein the monovalent cation salt is sodium chloride or potassium chloride.

17. The process of claim 16 wherein the suspension of step (e) is extruded through the orifice having a diameter of from about 0.2 to 0.8 mm.

18. The process of claim 16 wherein the transplant is a coated pancreatic islet, hepatic cell, neural cell, renal cortex cell, vascular endothelial cell, thyroid cell, adrenal cell, thymic cell or ovarian cell.

19. The process of claim 17 wherein the voltage of step (e) is DC voltage of from about 1 to about 400 KV.

20. The process of claim 17 wherein the solution capable of gelling and solidifying the alginate is an aqueous electrolyte solution containing calcium ions having concentration at least 0.5% by weight.

21. The process of claim 16 wherein the voltage difference between the needle tip and the droplet collector holding the gelling solution is at least $1 \times 10^{-6}$ newtons.

22. A process for producing a smooth, uniform and continuous polymer coating of living cell or tissue transplants intended to be implanted into the body of a host, wherein said coating is non-fibrogenic and has a uniform thickness from about 20 μm to about 200 μm, said process comprising the steps:
 (a) preparing a non-fibrogenic alginate containing less than 0.02 wt % fucose and less than 0.2 wt % of polyphenol by:
  (1) dissolving a nonpurified alginate polymer having a molecular weight from about 2 to about 300 Kda and a weight to weight ratio of mannuronate to mannuronate/guluronate (M/M+G) from about 0.1 to about 0.95, in an aqueous solution;
  (2) contacting said solution with a high surface area absorbent able to remove fucans and polyphenols;
  (3) separating the alginate polymer from the absorbent;
  (4) contacting the alginate polymer in solution with a monovalent cation; and (5) precipitating the alginate polymer from the solution;

(b) preparing an aqueous solution of the non-fibrogenic alginate precipitate of step (a);

(c) dispersing the tissue or cells in the solution of step (b) to form a suspension having a viscosity from about 50 to about 150 centipoises;

(d) transferring the suspension of step (c) to an electrostatic apparatus comprising a reservoir, an extrusion needle, an electroconductive droplet collector and a means for generating electrostatic field of opposite charge, said reservoir being used for holding the suspension and being in communication with the extrusion needle, said needle positioned above the electroconductive droplet collector containing a gelling solution, said means for generating electrostatic field being able to generate a sufficient electrostatic voltage to maintain the attenuated stream of the suspension due to an opposite charge between the extrusion needle and between the droplet collector;

(e) generating a DC electrostatic voltage level sufficient to maintain the attenuated stream of the suspension to form a continuous series of the charged droplets wherein said voltage is being generated between the needle tip and between the container holding the gelling solution;

(f) extruding the suspension of step (c) through an extrusion needle tip having an end orifice diameter of from about 0.1 to about 2 mm, in an attenuated stream into the gelling solution and solidifying the alginate polymer of step (c) to form the droplets having constant and reproducible size;

(g) maintaining said voltage level during the whole time of formation of the droplets to provide an electrostatic attraction of the gelling solution for the charged droplets;

(g) collecting the droplets coated with a gelled and solidified non-fibrogenic alginate of from about 20 μm to about 200μ thickness as the transplants.

23. The process of claim 21 wherein the transplant is a coated pancreatic islet, hepatic cell, neural cell, renal cortex cell, vascular endothelial cell, thyroid cell, adrenal cell, thymic cell or ovarian cell.

* * * * *